(12) United States Patent
Luxon et al.

(10) Patent No.: US 11,679,196 B2
(45) Date of Patent: *Jun. 20, 2023

(54) DEVICES AND METHODS FOR MANAGING CHEST DRAINAGE

(71) Applicant: Centese, Inc., Omaha, NE (US)

(72) Inventors: Evan S. Luxon, Omaha, NE (US); Daniel R. Burnett, San Francisco, CA (US); Mark Ziegler, Palo Alto, CA (US)

(73) Assignee: Centese, Inc., Omaha, NE (US)

( * ) Notice: Subject to any disclaimer, the term of this patent is extended or adjusted under 35 U.S.C. 154(b) by 511 days.

This patent is subject to a terminal disclaimer.

(21) Appl. No.: 16/892,098

(22) Filed: Jun. 3, 2020

(65) Prior Publication Data

US 2020/0289724 A1    Sep. 17, 2020

Related U.S. Application Data

(63) Continuation of application No. 15/422,323, filed on Feb. 1, 2017, now Pat. No. 10,702,634, which is a
(Continued)

(51) Int. Cl.
*A61M 1/00* (2006.01)
*A61M 27/00* (2006.01)
*A61M 25/00* (2006.01)

(52) U.S. Cl.
CPC ............. *A61M 1/743* (2021.05); *A61M 1/83* (2021.05); *A61M 27/00* (2013.01);
(Continued)

(58) Field of Classification Search
CPC ........ A61M 1/742; A61M 1/743; A61M 1/83; A61M 27/00; A61M 2025/0019;
(Continued)

(56) References Cited

U.S. PATENT DOCUMENTS 4,735,606 A   4/1988   Davison
4,762,130 A   8/1988   Fogarty et al.
(Continued)

FOREIGN PATENT DOCUMENTS

DE   202006006685   10/2006
JP   63-192457      8/1988
(Continued)

*Primary Examiner* — Benjamin J Klein
(74) *Attorney, Agent, or Firm* — Levine Bagade Han LLP

(57) ABSTRACT

Disclosed is a chest drainage system which reduces or eliminates pooling of blood/liquid and/or clogging/clotting in the drainage tube. Generally, the chest drainage system continuously monitors chest tube status and clears pooled liquid when necessary to restore negative pressure to the chest. The system may include a valve device which is located between the patient's chest tube and drainage tube and may be used with any standard chest tube. The chest drainage system also includes a controller for monitoring the pressure at or near the valve device and/or at or near the suction device, and possibly a pump for assisting in clearance of pooled liquid and/or clots. The controller may also control the valve device and/or suction device in response to pressure signals.

24 Claims, 12 Drawing Sheets

Related U.S. Application Data continuation of application No. PCT/US2015/052960, filed on Sep. 29, 2015.

(60) Provisional application No. 62/181,031, filed on Jun. 17, 2015, provisional application No. 62/149,559, filed on Apr. 18, 2015, provisional application No. 62/136,488, filed on Mar. 21, 2015, provisional application No. 62/056,683, filed on Sep. 29, 2014.

(52) U.S. Cl.
CPC ............... *A61M 2025/0019* (2013.01); *A61M 2205/106* (2013.01); *A61M 2205/3337* (2013.01); *A61M 2205/3344* (2013.01); *A61M 2205/50* (2013.01); *A61M 2205/502* (2013.01); *A61M 2205/52* (2013.01); *A61M 2210/101* (2013.01)

(58) Field of Classification Search
CPC .... A61M 2205/106; A61M 2205/3337; A61M 2205/3344; A61M 2205/50; A61M 2205/52; A61M 2210/101
See application file for complete search history.

(56) References Cited

U.S. PATENT DOCUMENTS

| | | |
|---|---|---|
| 5,188,618 A | 2/1993 | Thomas |
| 5,709,691 A | 1/1998 | Morejon |
| 5,738,656 A | 4/1998 | Wagner |
| 7,207,946 B2 | 4/2007 | Sirokman |
| 7,798,974 B2 | 9/2010 | Sirokman |
| 7,976,533 B2 | 7/2011 | Larsson |
| 8,070,735 B2 | 12/2011 | Koch et al. |
| 8,157,775 B2 | 4/2012 | Bobroff et al. |
| 8,226,620 B2 | 7/2012 | Giezendanner et al. |
| 8,418,868 B2 | 4/2013 | Hofmann et al. |
| 8,439,893 B2 | 5/2013 | Wakabayashi |
| 8,486,051 B2 | 7/2013 | Larsson |
| 8,491,550 B2 | 7/2013 | Ramella et al. |
| 8,529,530 B2 | 9/2013 | Koch et al. |
| 8,535,284 B2 | 9/2013 | Ramella et al. |
| 8,801,684 B2 | 8/2014 | Walti et al. |
| 8,808,260 B2 | 8/2014 | Koch et al. |
| 8,827,972 B2 | 9/2014 | Ehlert |
| 8,882,678 B2 | 11/2014 | Karwoski et al. |
| 8,992,493 B2 | 3/2015 | Croteau et al. |
| 9,314,599 B2 | 4/2016 | Karwoski et al. |
| 9,333,281 B2 | 5/2016 | Giezendanner et al. |
| 9,486,561 B2 | 11/2016 | Walti et al. |
| 10,702,634 B2 * | 7/2020 | Luxon ................... A61M 1/742 |
| 2010/0145201 A1 | 6/2010 | Westbrook et al. |
| 2012/0041334 A1 | 2/2012 | Goedje et al. |
| 2012/0059340 A1 * | 3/2012 | Larsson ................ A61M 1/743 |
| | | 604/319 |
| 2013/0172840 A1 | 7/2013 | Lampotang et al. |
| 2014/0100540 A1 | 4/2014 | Linder et al. |
| 2014/0194793 A1 | 7/2014 | Nakata et al. |
| 2014/0194835 A1 | 7/2014 | Ehlert |
| 2014/0213992 A1 | 7/2014 | Ehlert |
| 2014/0228781 A1 | 8/2014 | Boyle et al. |
| 2015/0174305 A1 | 6/2015 | Bharat |
| 2015/0320916 A1 | 11/2015 | Croteau et al. |
| 2016/0228622 A1 | 8/2016 | Linder et al. |
| 2017/0007749 A1 | 1/2017 | Walti et al. |
| 2021/0154378 A1 | 5/2021 | Luxon et al. |

FOREIGN PATENT DOCUMENTS

| | | |
|---|---|---|
| JP | 11-514271 | 12/1999 |
| JP | 2007-515192 | 6/2007 |
| JP | 2011-513024 | 4/2011 |
| JP | 2014-519930 | 8/2014 |
| WO | WO 2005/061025 | 7/2005 |
| WO | WO 2015/105828 | 7/2015 |

\* cited by examiner

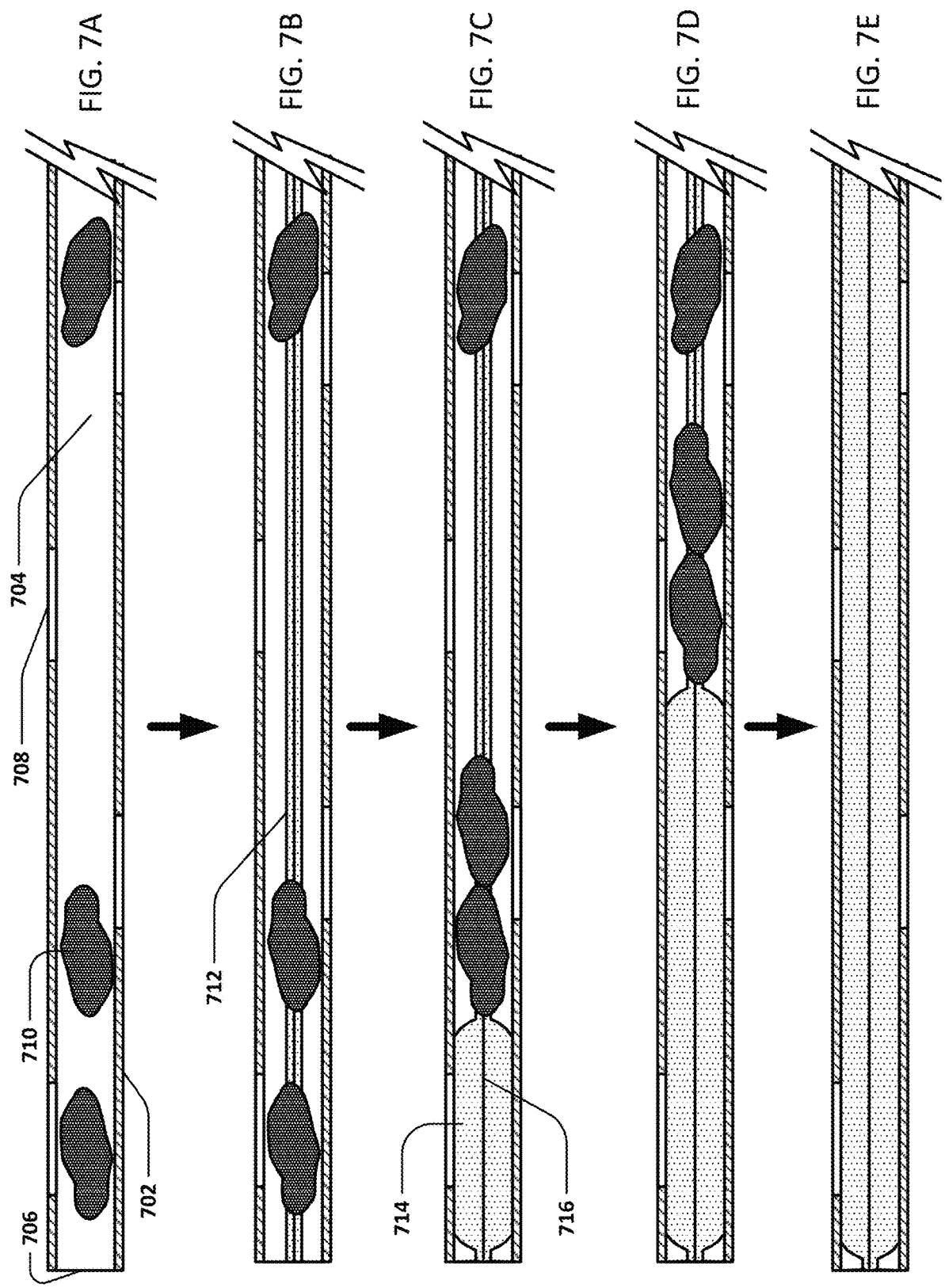

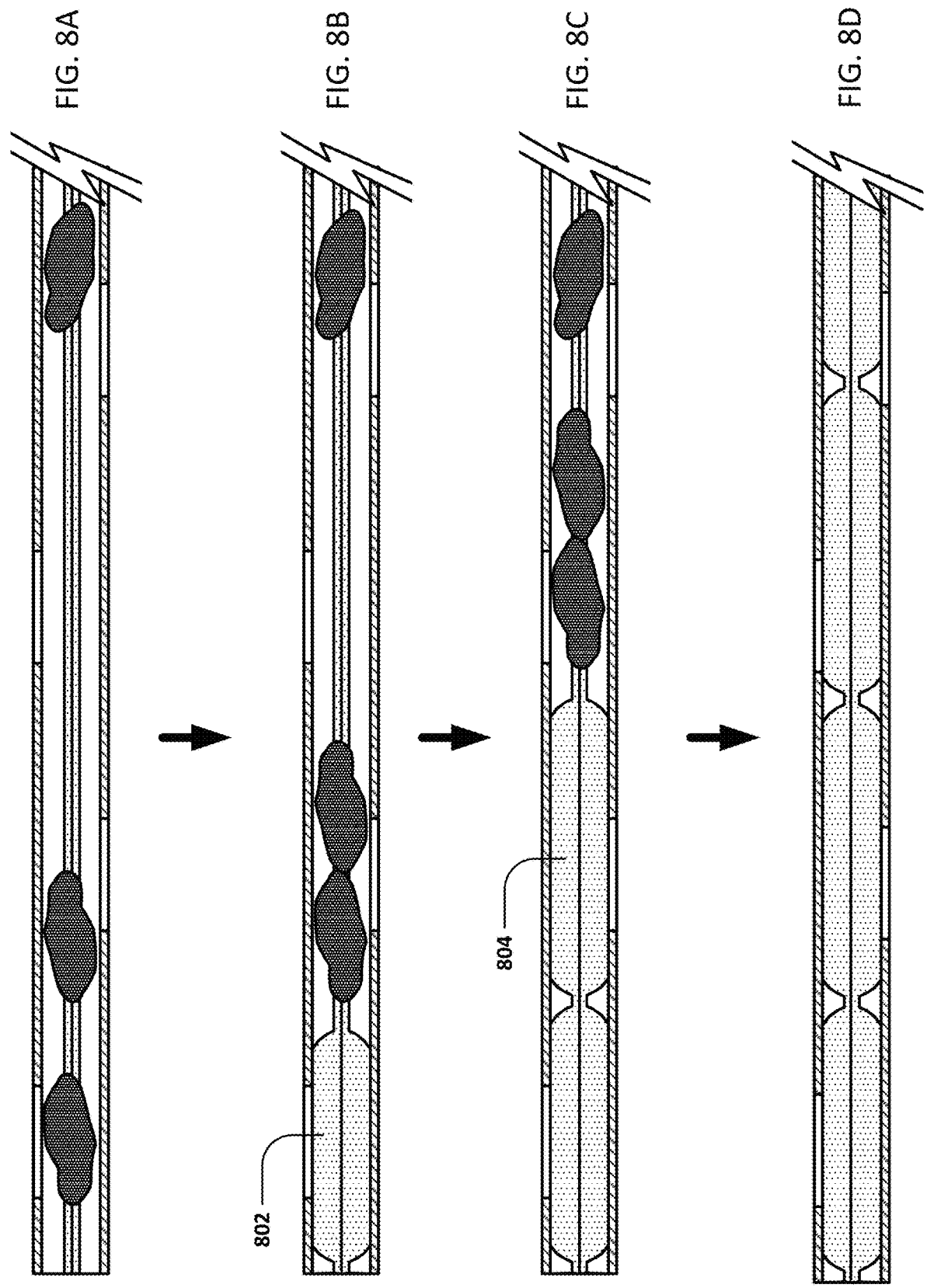

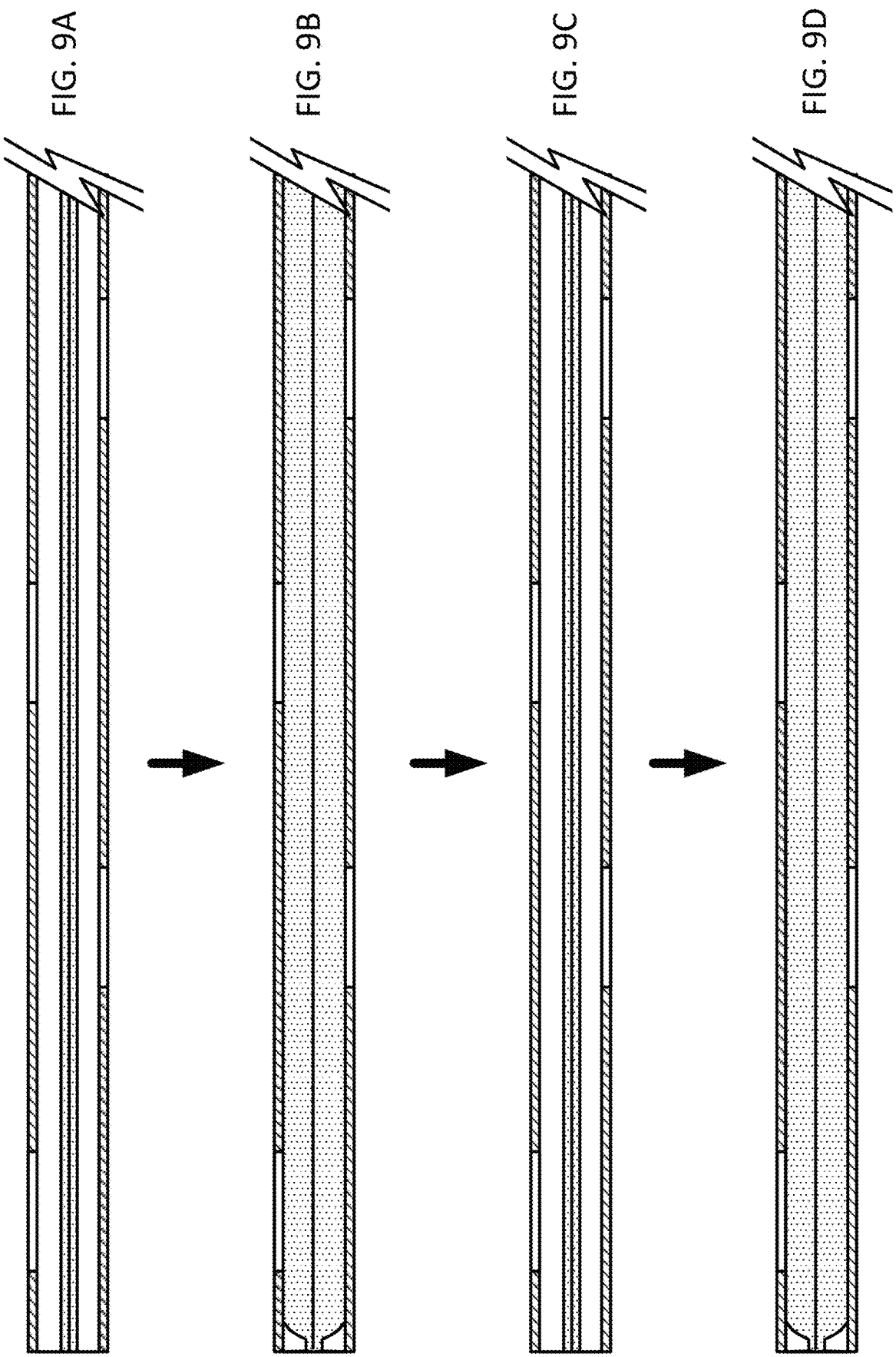

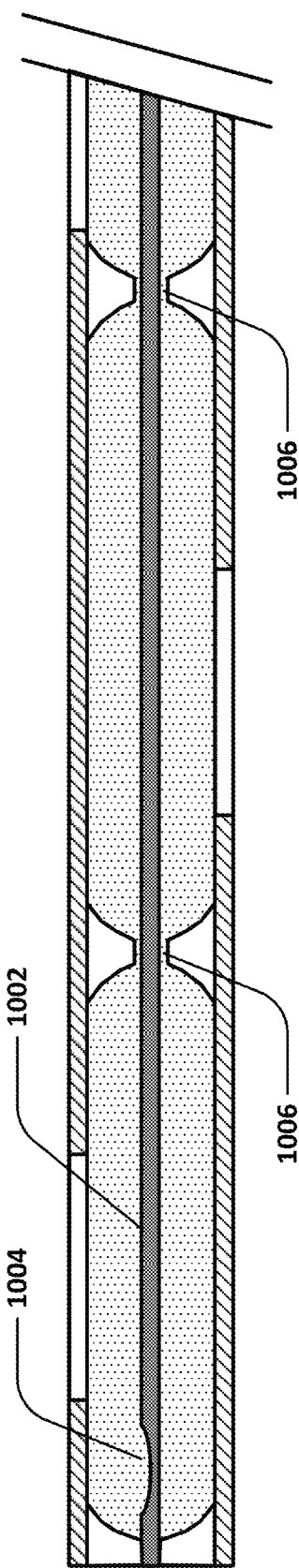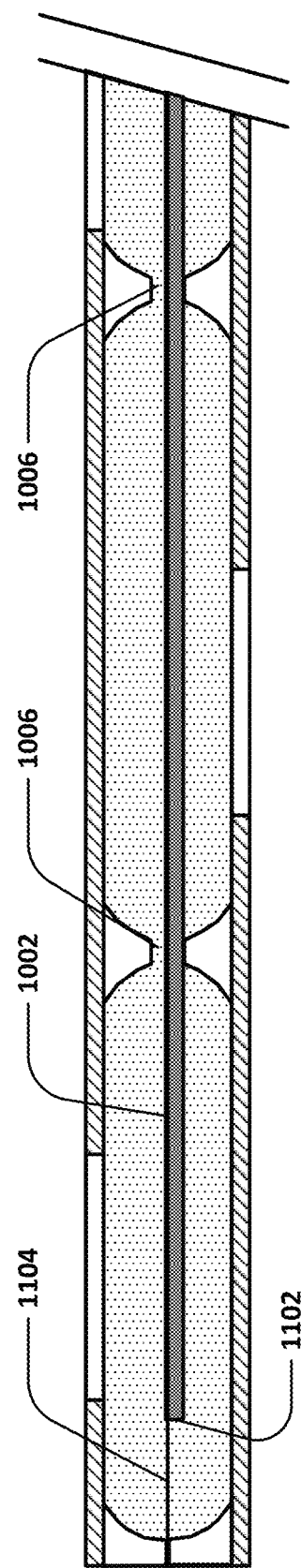

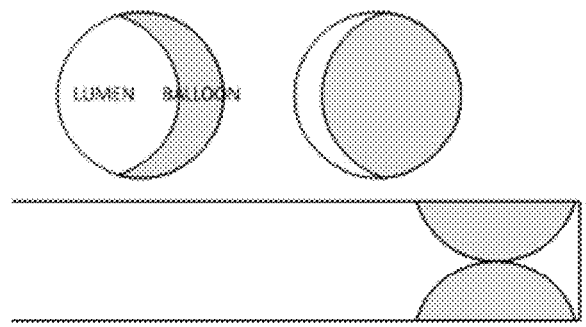
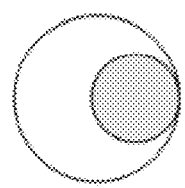
FIG. 12
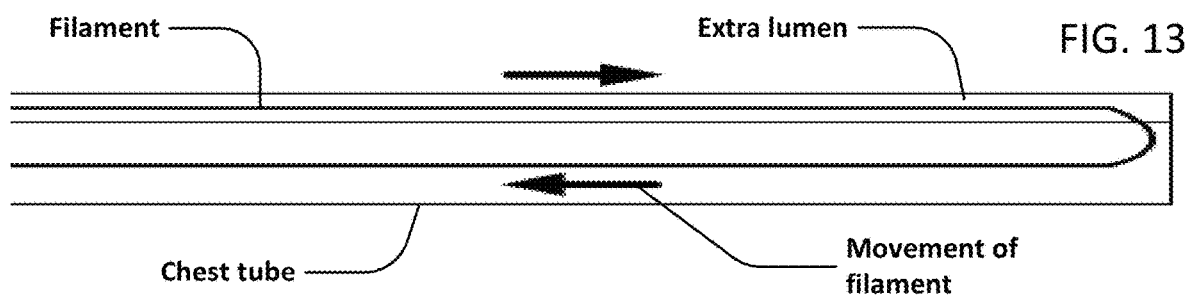
FIG. 13
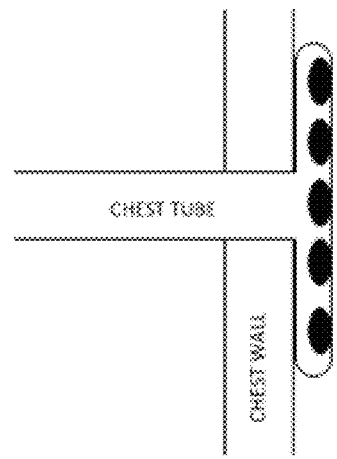
FIG. 14

DEVICES AND METHODS FOR MANAGING CHEST DRAINAGE

CROSS-REFERENCE TO RELATED APPLICATIONS

This application is a continuation of U.S. patent application Ser. No. 15/422,323 filed Feb. 1, 2017, which is a continuation of International Patent Application No. PCT/US2015/052960 filed Sep. 29, 2015, which claims the benefit of priority to U.S. Provisional Application No. 62/056,683 filed Sep. 29, 2014 and U.S. Provisional Application No. 62/136,488 filed Mar. 21, 2015 and U.S. Provisional Application No. 62/149,559 filed Apr. 18, 2015 and U.S. Provisional Application No. 62/181,031 filed Jun. 17, 2015, each of which is incorporated herein by reference in its entirety.

FIELD OF THE INVENTION

The present invention relates to wound and surgical drainage.

INCORPORATION BY REFERENCE

All publications and patent applications mentioned in this specification are herein incorporated by reference to the same extent as if each such individual publication or patent application were specifically and individually indicated to be so incorporated by reference.

BACKGROUND OF THE INVENTION

Chest tubes are required anytime air or liquid accumulates in the chest cavity, disrupting normal pulmonary or cardiac function. Suction is applied continuously to remove any air or fluid from the chest until the internal leaks have sealed, at which point the chest tubes can be removed. One of the most common uses of chest tubes is to drain the area around the heart after cardiac surgery.

Despite their benefits, current chest tube systems suffer from two major flaws. First, as liquid drains from the chest toward the suction container, it can pool in the drainage tubing and prevent the applied negative pressure from being transmitted to the chest. When this occurs, the pressure in the chest can be reduced to zero or even become positive. Second, clogs can form that obstruct the chest tube, which prevent the negative pressure from being transmitted to the chest and inhibit drainage. In fact, 36% of cardiac surgery patients experience chest tube clogging. When proper drainage is inhibited due to these factors, patients are at increased risk for accumulation of fluid around the heart, known as pericardial tamponade, which results in shock and can be fatal. Additionally, the lungs may be compressed, which can lead to respiratory compromise and be fatal as well.

Pooling of liquid in the drainage line can theoretically be remedied by keeping the tubing straight from the patient to the collection container. However, this is nearly impossible in practice, as some slack is required to prevent accidental dislodging of the tube from the body. To combat clogging, clinicians use two methods known as milking and stripping. Milking refers to line manipulations such as lifting, squeezing, or kneading. Stripping refers to a pulling along the length of the tube with the thumb and forefinger to increase the amount of suction at the end of the tube. However, these methods have not been shown to be effective at improving chest tube suction or drainage. In fact, stripping has actually been discouraged because it is possible to create extremely high negative pressures (up to −370 cmH$_2$O) that may damage the tissue.

SUMMARY OF THE INVENTION

A chest drainage system is needed which reduces or eliminates pooling of blood/liquid and/or clogging/clotting in the drainage tube.

One embodiment of the drainage system may generally comprise a suction device configured to generate a negative pressure, a first lumen body configured for insertion into a patient body, a second lumen body fluidly coupled to the suction device, a valve assembly fluidly coupled to the first lumen body and to the second lumen body, wherein the valve assembly includes at least a first valve having a closed configuration where the negative pressure generated by the suction device is maintained within the second lumen body, and the first valve further having an open configuration where the negative pressure draws air from an environment and through the second lumen body, a pressure sensor in communication with the first lumen body, and a controller in communication with the pressure sensor, wherein the controller is programmed to sense for a decrease in the negative pressure indicative of an obstruction within the second lumen body, wherein the controller is further programmed to actuate the first valve into the open configuration upon sensing the decrease to clear the obstruction. In another embodiment, the valve may have certain mechanical characteristics, including but not limited to crack pressure, such that it automatically open when the negative pressure decreases a certain amount, eliminating the need for the pressure sensor and controller.

Another embodiment of the drainage system may generally comprise a suction device configured to generate a negative pressure, a first lumen body configured for insertion into a patient body, a second lumen body fluidly coupled to the suction device, a valve assembly fluidly coupled to the first lumen body and to the second lumen body, wherein the valve assembly includes at least a first valve having a closed configuration where the negative pressure generated by the suction device is maintained within the second lumen body, and the first valve further having an open configuration where the negative pressure draws air from an environment and through the first lumen body, a pressure sensor in communication with the first lumen body, and a controller in communication with the pressure sensor, wherein the controller is programmed to sense for a decrease in the negative pressure indicative of an obstruction within the first lumen body, wherein the controller is further programmed to actuate the first valve into the open configuration upon sensing the decrease to clear the obstruction. In another embodiment, the valve may have certain mechanical characteristics, including but not limited to crack pressure, such that it automatically open when a certain pressure differential exists between the first and second lumen bodies, eliminating the need for the pressure sensor and controller.

In one exemplary method of use, the method for draining a body lumen may generally comprise applying a negative pressure to a first lumen body inserted into a patient body, drawing a fluid from the patient body via the first lumen body and through a second lumen body in fluid communication with the first lumen body, monitoring via a pressure sensor for a decrease in the negative pressure as indicative of an obstruction within the second body lumen, actuating a valve assembly coupled to the first lumen body and to the second lumen body upon detecting the decrease such that at least a first valve in the valve assembly actuates from a closed configuration, where the negative pressure is maintained within the second lumen body, and into an open configuration, where the negative pressure draws air from an environment and through the second lumen body, and clearing an obstruction from the second lumen body via the air introduced into the second lumen body. In another exemplary method of use, the valve may automatically open when the negative pressure decreases by a certain amount, eliminating the need to monitor pressure and actuate the valve.

In another exemplary method of use, the method for draining a body lumen may generally comprise applying a negative pressure to a first lumen body inserted into a patient body, drawing a fluid from the patient body via the first lumen body and through a second lumen body in fluid communication with the first lumen body, monitoring via a pressure sensor for a decrease in the negative pressure as indicative of an obstruction within the first body lumen, actuating a valve assembly coupled to the first lumen body and to the second lumen body upon detecting the decrease such that at least a first valve in the valve assembly actuates from a closed configuration, where the negative pressure is maintained within the second lumen body, and into an open configuration, where the negative pressure draws air from an environment and through the first lumen body, and clearing an obstruction from the first lumen body via the air introduced into the first lumen body. In another exemplary method of use, the valve may automatically open when a pressure differential exists between the first and second lumen bodies eliminating the need to monitor pressure and actuate the valve.

BRIEF DESCRIPTION OF THE DRAWINGS

FIGS. 7A-7E show an embodiment of the chest drainage system relating to clearing of a chest tube.

FIGS. 8A-8D show an embodiment of the chest drainage system relating to clearing of a chest tube.

FIGS. 9A-9D show an embodiment of the chest drainage system relating to clearing of a chest tube.

FIG. 10 shows an embodiment of the chest drainage system relating to clearing of a chest tube.

FIG. 11 shows an embodiment of the chest drainage system relating to clearing of a chest tube.

FIGS. 12-14 show other embodiments of the chest drainage system.

DETAILED DESCRIPTION OF THE INVENTION

Disclosed is a chest drainage system which reduces or eliminates pooling of blood/liquid and/or clogging/clotting in the drainage tube.

The chest drainage system continuously monitors chest tube status and clears pooled liquid when necessary to restore negative pressure to the chest. The system may include a valve device which is located between the patient's chest tube and drainage tube and may be used with any standard chest tube. The chest drainage system also includes a controller for monitoring the pressure at or near the valve device and/or at or near the suction device, and possibly a pump for assisting in clearance of pooled liquid and/or clots. The controller may also control the valve device and/or suction device in response to pressure signals. The chest drainage system performs four primary functions:

1. The chest drainage system detects pooled liquid in the drainage tube by monitoring the pressure near the patient-external end of the chest tube. Pooled liquid is indicated by a decrease in vacuum (increasing pressure). The chest drainage system measures pressure with a sensor on or near the valve device. The valve device includes a vent or valve which prevents the transmission of bacteria and viruses.

2. When pooled liquid is detected, the chest drainage system clears the drainage tube by opening a valve in the valve device to allow sterile air to sweep away the liquid into the drainage container. Optionally the pump may also be activated to apply positive pressure between the chest tube and drainage system and/or negative pressure at the collection container. Proper negative pressure at the chest is then restored, which prevents clogs from forming in the chest tube.

3. In the event that clots or clogs do form, the chest drainage system detects clogs in the chest tube by monitoring the pressure in the drainage tube. The chest drainage system intermittently closes the drainage tube via the valve device and checks for pressure fluctuations due to respirations, which are present in the absence of clogs.

4. In the event that clots or clogs are present, the chest drainage system may additionally clear the clots/clogs.

The suction device of the chest drainage system connects to the patient's bed and houses the electronics, including possibly the controller. The valve device may be disposable and connects to the chest tube on one end and the drainage tube on the other.

In another embodiment, the valves are mechanical tuned to activate at certain pressures, eliminating the need for the pressure sensor and controller.

Figure 1:
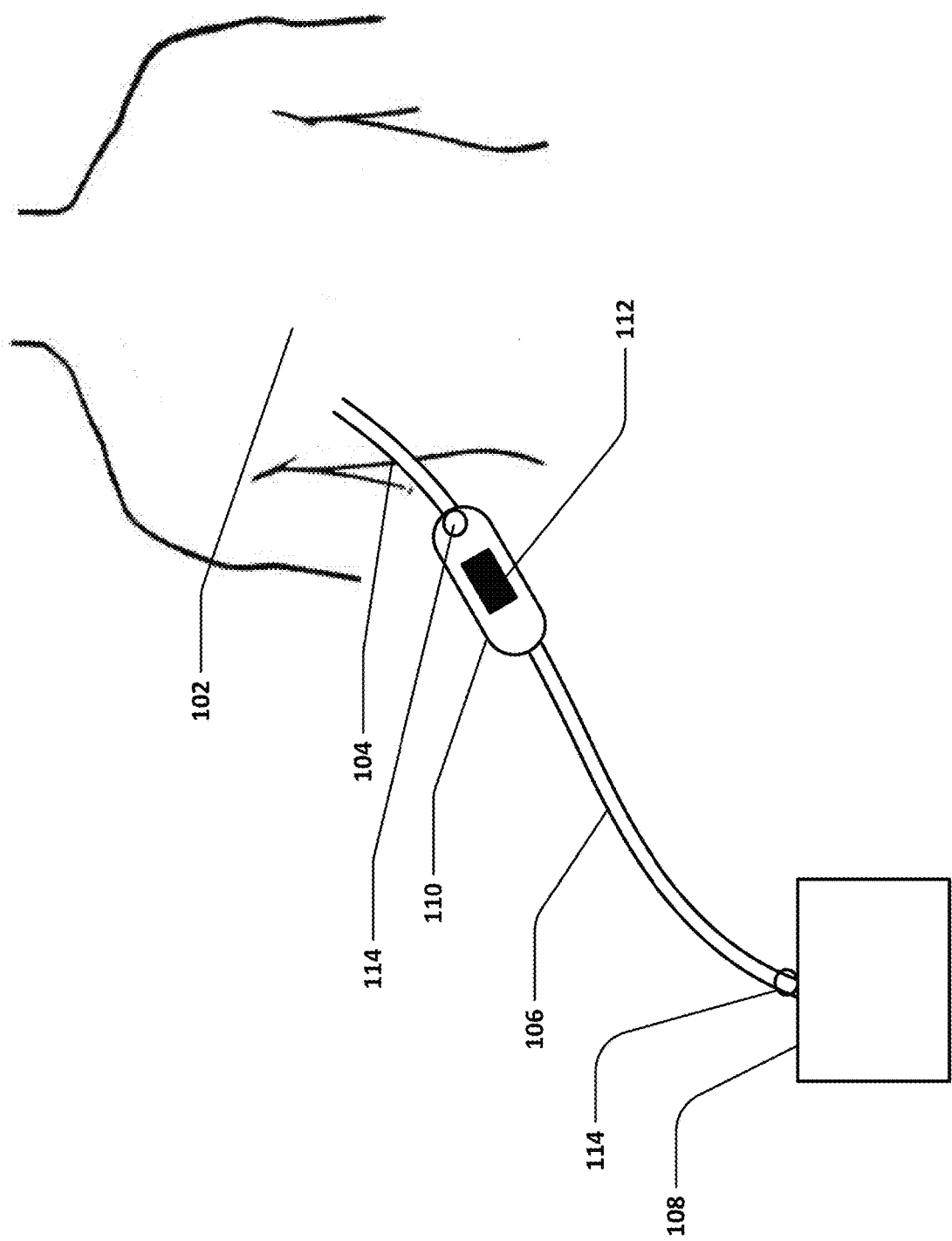
FIG. 1 shows an embodiment of the chest drainage system.

FIG. 1 shows an embodiment of the chest drainage system. Patient chest 102 is drained using the system. Chest tube 104 is in direct fluid communication with the chest cavity. Drainage tube 106 is in fluid communication with suction device 108. Valve device 110 which includes vent/valve 112 is between chest tube 104 and drainage tube 106. Valve device 110 is in fluid communication with both chest tube 104 and drainage tube 106. Valve device 110 may be controlled by a controller or may be controlled manually. The valve device may be used to periodically close off fluid flow from the chest tube and/or open vent/valve 112 to allow air to enter the drainage tube and clear any obstructions or slow fluid flow in the drainage tube. The valve device may also be used with an additional internal lumen in the chest tube to allow air to enter the proximal end of the chest tube and clear any obstructions into the drainage tube. The valve device may also include a pump to assist with drainage. This clearing action may be performed on a periodic basis, as with a timer, or may be performed in response to a signal that the drainage tube and/or chest tube is not flowing freely.

Pressure sensor(s) 114 may reside at various locations in the system. Here, a pressure sensor is shown near chest tube 104 and also near suction device 108. Pressure sensors may also be located in other places in the system, for example, near the chest. Pressure sensed at one or more location is used to determine whether there is an impediment to fluid flow through the system. If an impediment is detected, an audible alarm may sound, and/or the controller may automatically control the valve device to clear the drainage tube and/or chest tube. More detail on this is provided below.

Suction device 108 creates a negative pressure, or suction, force on the drainage tube which is in fluid communication with the valve device and chest tube. In this way, suction may be maintained on the chest cavity to promote chest fluid drainage and aid with patient breathing. The mechanism for creating the negative pressure may be a pump or any other suitable mechanism.

The controller (not shown) may be incorporated into the suction device and/or the valve device and/or be separate. Any communication between the controller and the suction device and/or valve device may be wired or wireless.

Figure 2A:
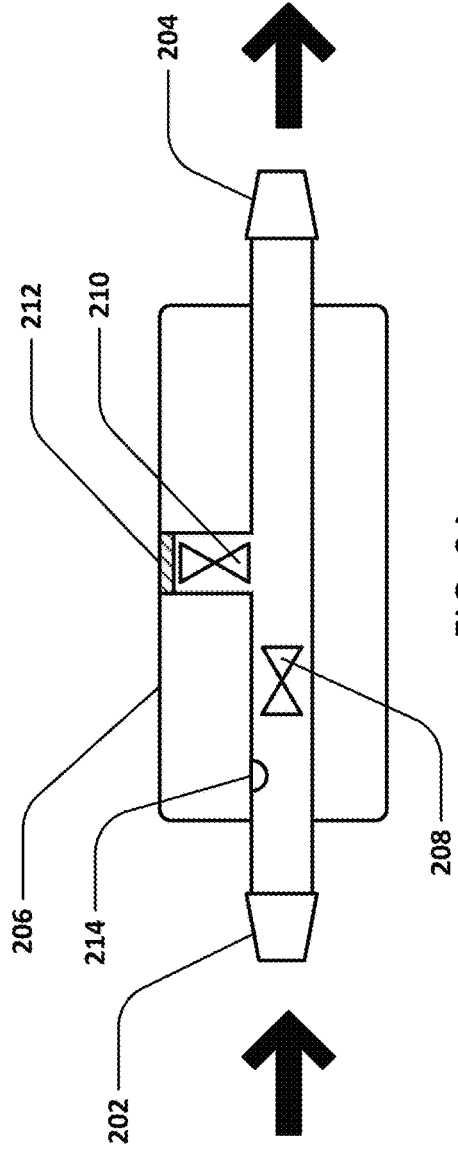
FIG. 2A shows an embodiment of the valve device.

FIG. 2A shows an embodiment of the valve device. Connector 202 connects to the chest tube. Connector 204 connects to the drainage tube. During normal operation, blood and other fluids flow freely through the valve device in the direction of the arrows. Valve 208 is normally open and valve 210 is normally closed. If an impediment to fluid flow is detected, valve 210 may be opened to allow atmospheric or other air to enter the system through vent 212. Vent 212 prevents contaminates in the air from entering the inner lumen of the valve device and therefore the fluids within the system remain sterile. Because negative pressure is being applied to connector 204 via the suction device, air will flow through the system and clear the drainage line. Valve 210 may then be closed to allow for normal drainage. The opening and closing of valve 210 may be performed manually, or automatically via control of the controller based on the measured pressures in the system, or automatically based on mechanical characteristics of the valve, including but not limited to crack pressure. Multiple openings and closings of valve 210 may be necessary to clear the line. Valve 208 may or may not be closed during the clearing process, or may be closed for part of the clearing process. When valve 208 is closed, all the negative pressure created by the suction device is applied to the drainage tube and will be used to allow air to enter and clear the system. When valve 208 is open, some of the negative pressure will be applied to the chest tube which may aid in clearing any clots/obstructions in that area. Valve 208 may only be opened if the obstruction is not cleared by opening valve 210 alone. When valve 208 is open, care must be used to make sure the chest is not exposed to too much negative pressure which could cause injury. When valve 208 is closed, higher magnitude negative pressure can be used to clear any blockage if necessary. Optionally, when valve 208 is closed and valve 210 is open, the pump may apply positive pressure across vent 212 to assist with drainage.

Also shown in FIG. 2A is container 206 which houses the various components of the valve device, and pressure sensor 214, which may be incorporated into the valve device.

The valves may be any suitable type of active valve, such as a pinch valve, solenoid valve or ball valve. The valves may alternatively be passive valves, such as one-way valves, pinch valves, check valves, etc. For example a passive one-way valve or valves may be used which allows chest drainage when suction is applied to the tube, but passively closes off to prevent flow into the chest when positive pressure is applied to the tube.

Figure 2B:
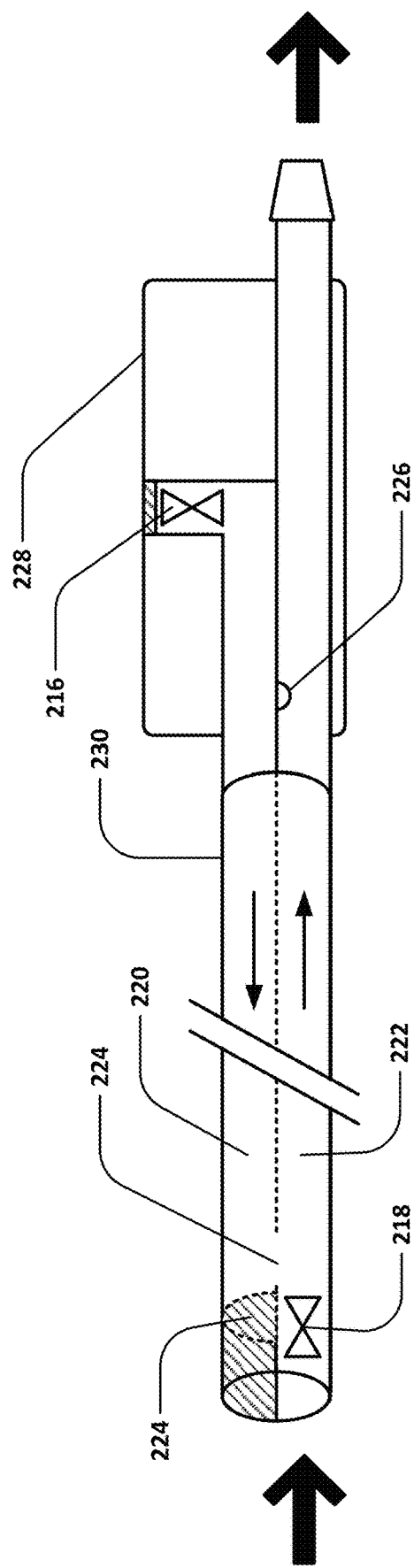
FIG. 2B shows an embodiment of the valve device in use with an embodiment of a chest tube.

FIG. 2B shows an embodiment of the valve device in use with an embodiment of a chest tube. This embodiment is used to clear a blockage in the chest tube. Valve device 228 includes valve 216 with filter and optional pressure sensor 226. Chest tube 230 is connected to valve device 228 so that the two lumens of the chest tube are in fluid communication with the lumens of the valve device. Lumen 220 carries air toward the patient. Lumen 222 carries blood/fluids away from the patient. The non-patient side of valve device 228 is connected to a drainage tube and a source of negative pressure. Opening 224 allows fluid communication between lumen 220 and lumen 222. A valve may or may not exist in opening 224. Lumen 222 is open on the patient end so that blood/fluids can drain from the patient. Lumen 220 is closed at patient end shown here as air lumen end 224. Optional valve 218 may be controlled by the controller to close off lumen 222 to the chest/body cavity so that air is prevented from entering the patient cavity.

When a blockage is present in the chest tube, either detected via pressure sensor 226 or otherwise, valve 216 is opened to allow air or gas, from the atmosphere or otherwise, to enter lumen 220. Negative pressure applied to lumen 220 may also be increased by the controller. The opening of valve 216 allows air/gas to enter the system and urges the contents of lumen 222 to travel away from the patient and through the chest tube and into the drainage tube (not shown here). After the chest tube blockage is cleared, either as sensed by pressure sensor 226 or automatically or manually, valve 216 is again closed and valve 218, if it is present, is again opened. If the negative pressure was increased, it is again decreased and fluid can again flow freely through lumen 222 and into the drainage tube. Valve 216 and valve 218 may be controlled by the controller or function automatically or manually. Wired communication between the controller and valve 218 may exist within a lumen of the chest tube or embedded within a wall of the chest tube. Communication between any of the valves and the controller may also be wireless. Valve 216 may open automatically based on pressure differentials across the valve. Valve 218, which may or may not be present, may also close automatically based on pressure differentials across the valve.

Figure 3:
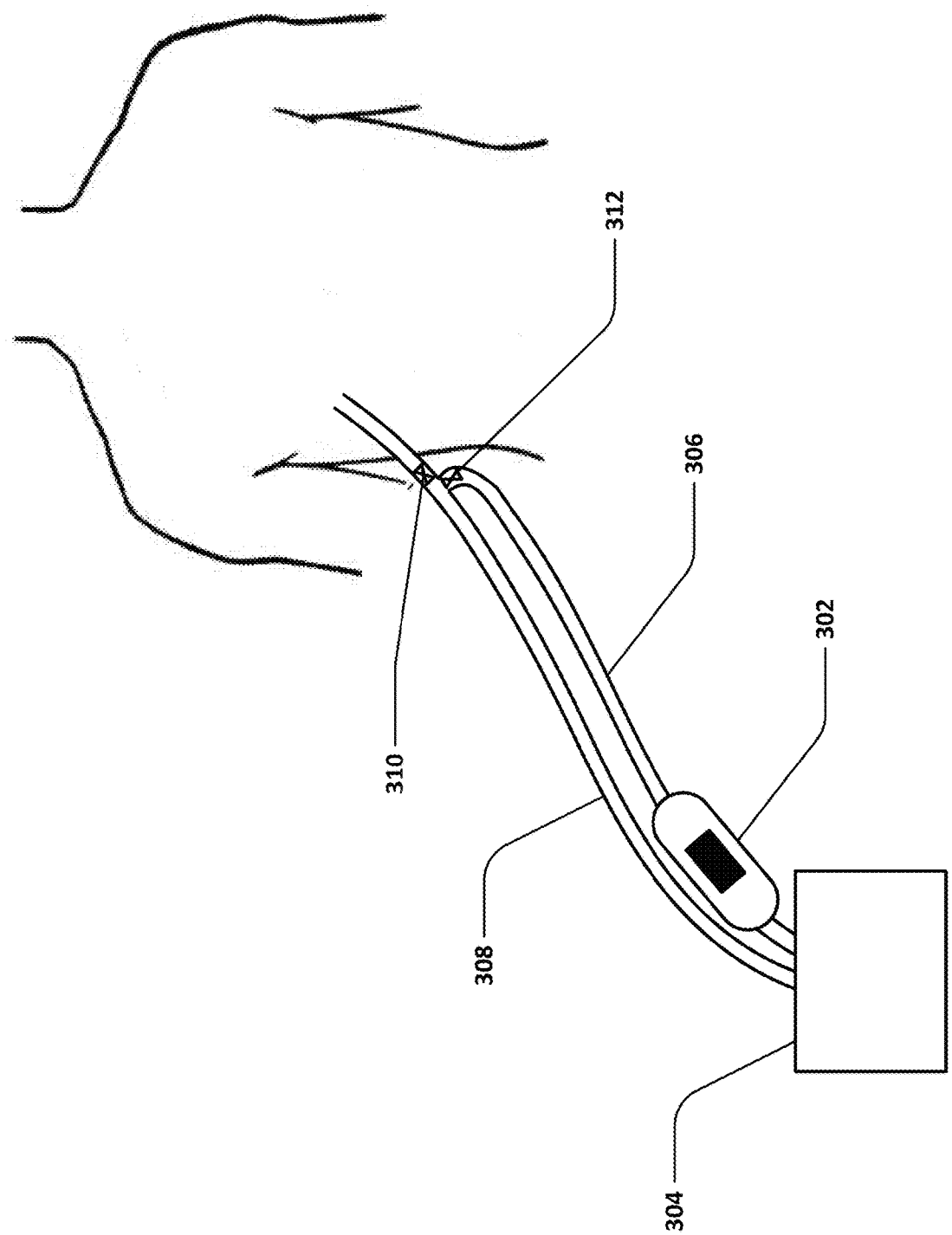
FIG. 3 shows another embodiment of the chest drainage system

FIG. 3 shows another embodiment of the chest drainage system. In this embodiment valve device 302 is located near, or incorporated into, suction device 304. The valve device is connected to a separate tube, valve tube 306. Pressure sensor(s) (not shown) may be located anywhere in the system, including near the chest and/or chest tube. If drainage tube 308 becomes blocked, as sensed by the pressure sensor(s), valve 312 is opened to allow clearing of the line. Valve 310 may also be closed, analogously to valve 208 in FIG. 2A. If a pump is used, it can assist with drainage by pumping through valve tube 306 and drainage tube 308 back into the collection container. Alternatively, the suction within the container may be controlled by the device, increasing in vacuum magnitude when valve 312 is open and valve 310 is closed in order to clear the drainage line. Valves 310, 312, valve device 302 and suction device 304 are controlled by a controller which may be incorporated into the suction device and or valve device, or may be separate. Communications with the controller may be wired or wireless.

Figure 4:
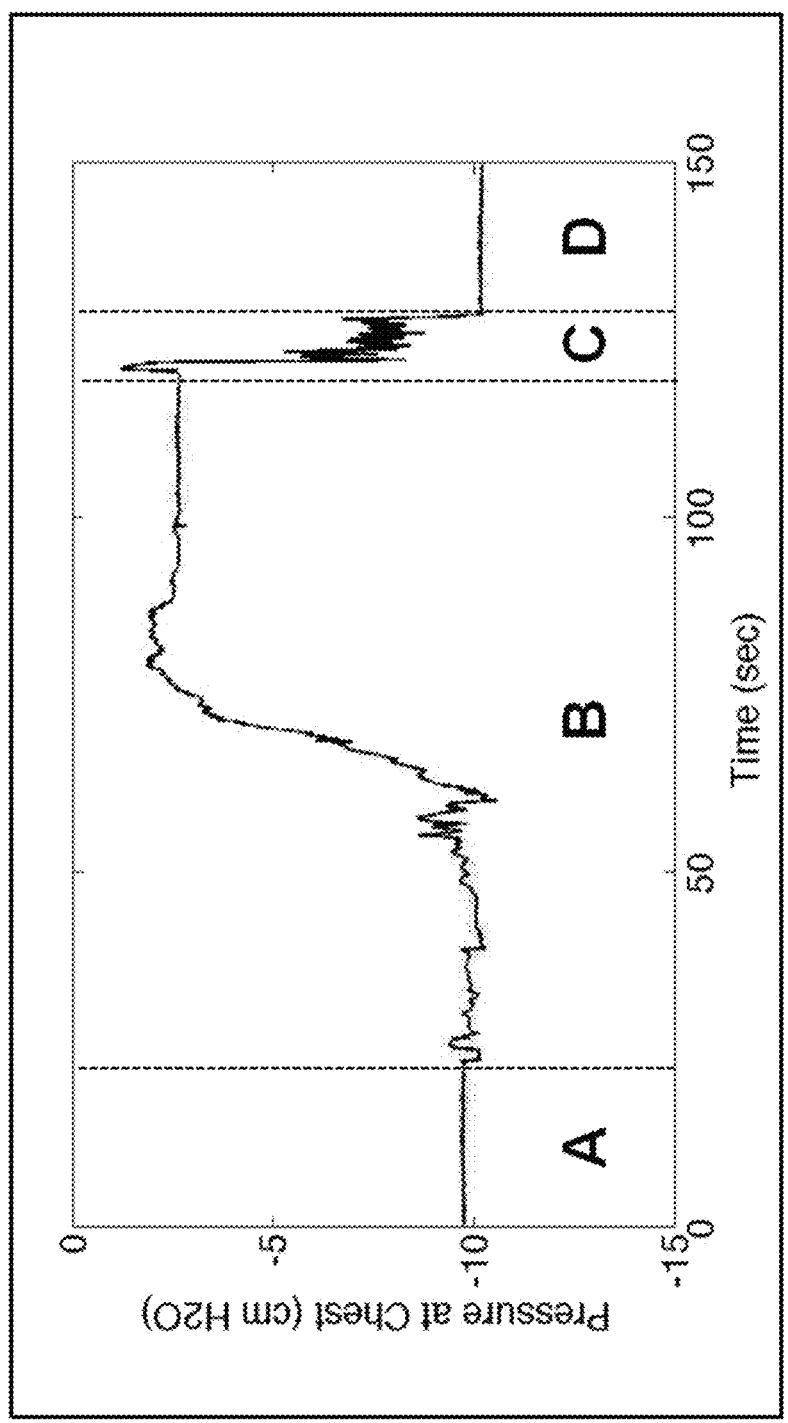
FIG. 4 shows the chest drainage system's ability to detect and clear pooled liquid in the drainage tube.

FIG. 4 shows the chest drainage system's ability to detect and clear pooled liquid in the drainage tube. In section 'A', −10 cmH2O of pressure is properly transmitted to the chest. In section 'T', liquid begins to pool in the bottom of the tube, resulting in a decreased negative pressure. If unresolved clinically, drainage would be impeded. However, in section 'C' a valve in the valve device is opened and the liquid is flushed into the drainage container, resulting is restoration of proper suction in Section 'D'. In this example, the pressure sensor is at or near the chest or chest tube. However pressure may be measured in other and/or additional locations in the system. For example, pressure may be measured at or near the chest or chest tube and also at or near the suction device, and the differential pressure measurement may be used to detect flow impediments or pooling or clotting of blood/fluid.

In this way, the controller can identify impediments to fluid drainage via the absolute pressure, change in pressure, pressure differential between or among 2 or more locations etc. When an impediment to fluid drainage is identified, an alarm may sound and/or the controller may initiate clearing procedures, including opening and/or closing valve(s) in the valve device, as described elsewhere herein. The negative pressure may be increased, or changed in other ways, such as pulsed, reversed etc.

For example, if a pressure sensor near the chest is reading around −10 cmH2O to around −20 cmH2O and the reading changes to zero to −5 cmH2O, the controller may open the valve to air in the valve device. The controller may also close the valve to the chest tube in the valve device. The controller may leave the valves in this position for a set period of time, say 5-10 seconds or 10-30 seconds and then may return the valves to their regular positions. The controller will then check the pressure readings and if they have returned to normal, do nothing more. If they have not returned to normal, indicating a blockage or slowing condition is still present, the controller may repeat the clearing procedure. This may be done repeatedly until the tubing is cleared. Alternatively or additionally, the procedure may change if repeat clearings are necessary. For example, the magnitude of negative pressure used by the suction device to clear the tubing may be increased, and/or the negative pressure may be pulsed. The clearing procedure may be performed in response to the pressure readings or it may be done automatically on a periodic basis.

Figure 5:
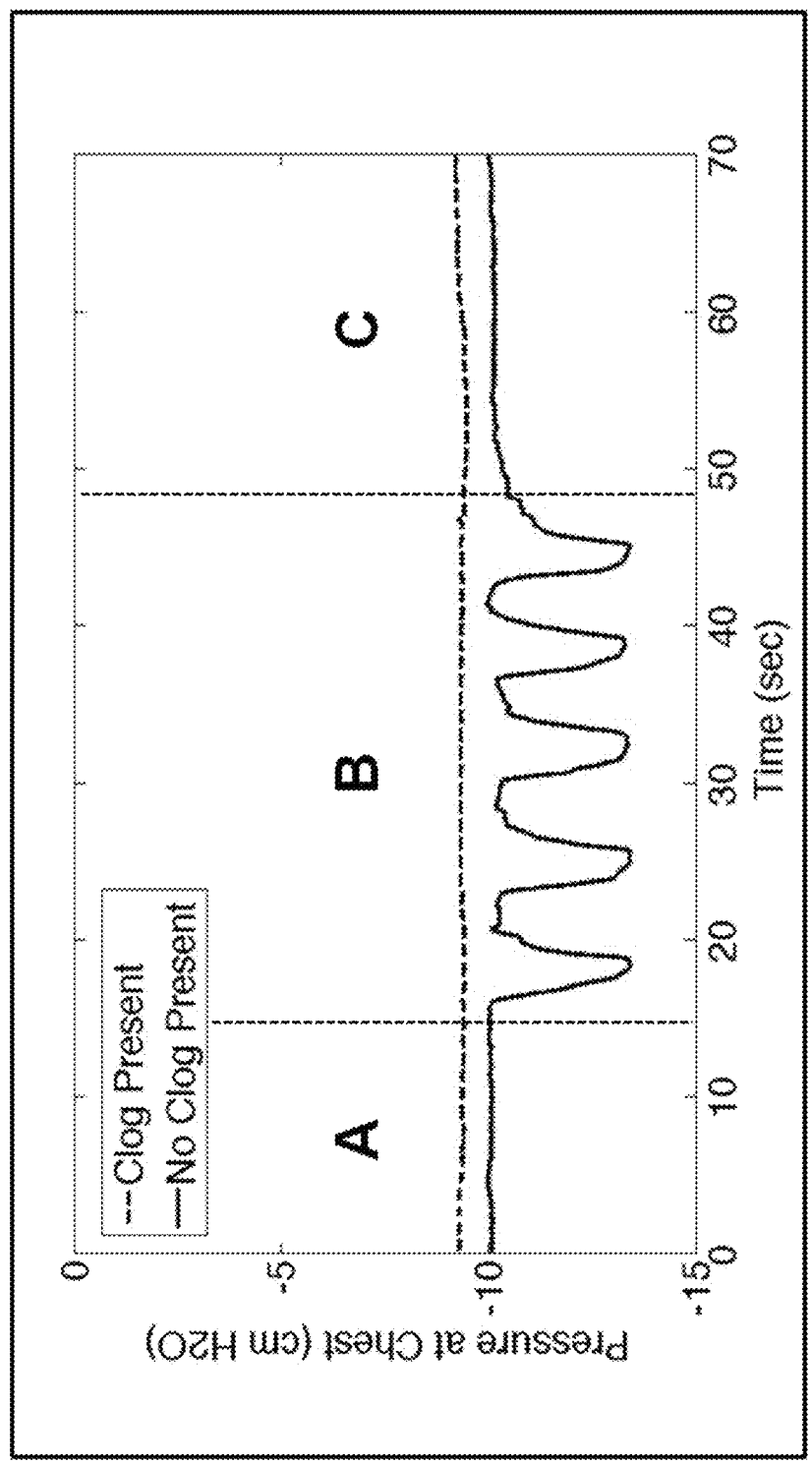
FIG. 5 shows the chest drainage system's ability to detect clogs in the chest tube.

FIG. 5 shows the chest drainage system's ability to detect clogs in the chest tube. In sections 'A' and 'C' normal suction is applied. In section 'B', the chest drainage system has entered clog detection mode and is watching for pressure fluctuations in the drainage system due to respirations. When no clog is present, the fluctuations are clearly seen, but when a clog is present, fluctuations are no longer observed. When a clog is detected, the chest drainage system sounds an alarm to alert the clinician, allowing for timely intervention. Alternatively, the chest drainage system automatically begins clog/clot elimination procedures. These procedures may include draining the drainage tube, as discussed elsewhere herein. In addition, these procedures may include applying energy to the chest tube and or the fluid column, including ultrasonic energy, vibrational energy, sound energy, mechanical energy, squeezing energy etc. The energy may be provided by the pump motor or may be provided by another source or sources.

The chest drainage system is of particular importance with pediatric patients. The amount of suction applied to the chest in adults is around −20 cmH2O, but with children it is limited to around −10 cmH2O to avoid damaging their more fragile tissues. With less suction, it is more difficult to clear pooled liquid or clots. Therefore the chest drainage system may be even more beneficial with pediatric patients.

Figure 6:
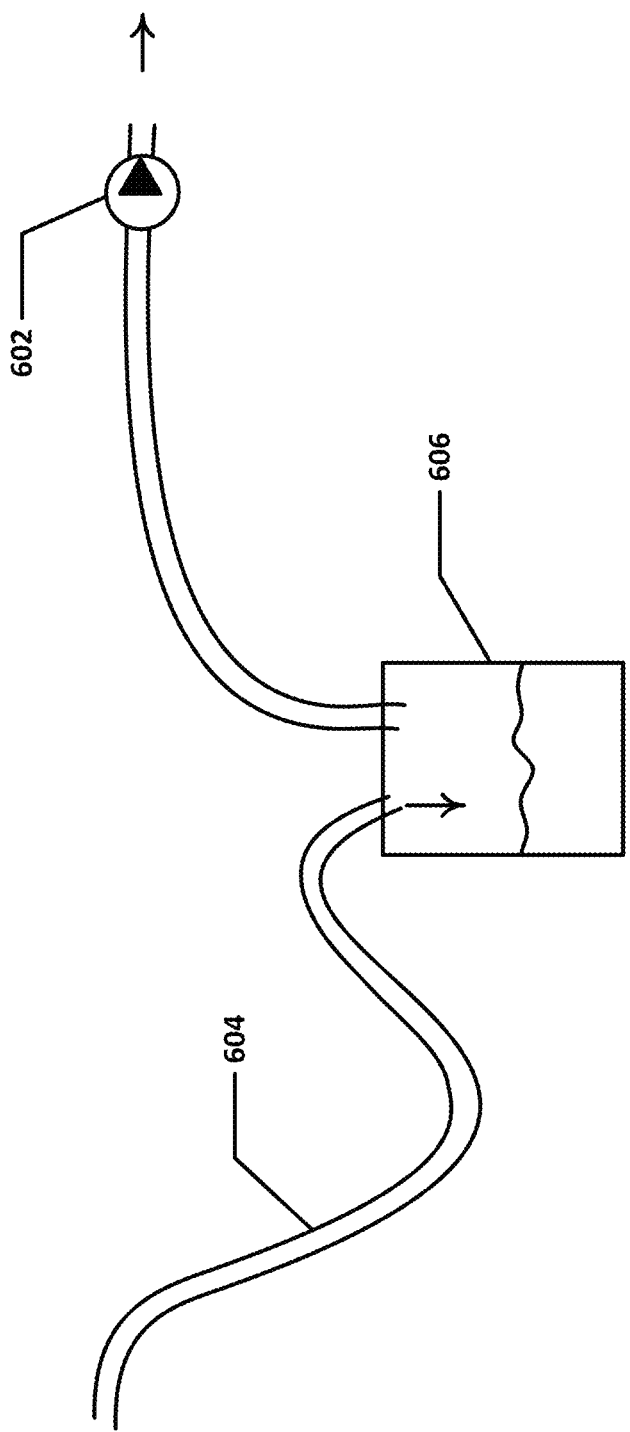
FIG. 6 shows an embodiment of a suction device.

FIG. 6 shows an embodiment of a suction device. Pump 602 pumps in the direction of the arrow to create negative pressure in the system. Drainage tube 604 is connected to fluid collection reservoir/container 606.

The chest drainage system may be used in conjunction with a hospital's own drainage and/or chest tubes. More than one chest tube and/or drainage tube may be employed by the system. In the case of multiple chest tubes, the tubes may utilize shared or separate drainage tubes. If separate, the chest drainage system may monitor pressure and activate clearing procedures and/or sound alarms on the drainage tubes individually. Alternatively, more than one chest tube may be connected to one valve device. One suction device may be used with multiple valve devices.

The chest drainage system may also include a chest tube which is designed to aid in clearing clots in the chest tube. For example, the chest tube may include an inflatable balloon or bladder which pushes fluid and clots toward the drainage end of the tube. The chest tube may include a mechanical device which automatically or manually pushes fluid and clots toward the drainage end of the tube. The chest tube may include more than one tube, either coaxial or otherwise which can be moved either longitudinally or radially with respect to each other or both. For example, the chest tube may include a tube within its drainage lumen which can be moved with respect to the drainage lumen to dislodge clots and return flow within the lumen to normal. This movement may be manual or automatic, and may be of small magnitude, such as a vibrational movement, or may be of a larger magnitude, such as 1-10 mm or 1-3 cm. The energy to move the tubes may be provided by the pump motor of the pump device.

In some embodiments, the pump device may be incorporated into the valve device. This combination device may be at the drainage end of the drainage tube, or may be between the chest tube and the drainage tube. It may alternatively be incorporated into the chest tube.

In some embodiments, the chest drainage system may include a pH sensor. Post-surgery infection and empyema are of particular concern to clinicians. The pH of fluid drained from the body can be useful in diagnosing these, and other, conditions. To aid in the diagnosis, the chest drainage system may include a pH monitor in the tubing, the pump, the valve device, or anywhere in the system. The results may be displayed on the display device.

FIGS. 7A-E show an embodiment of the chest drainage system which includes a balloon for dislodging clots and/or clogs in the chest tube. FIG. 7A shows the end of a chest tube which is placed into the chest of a patient. Some, or all, of this portion of a chest tube may be the chest of a patient. Chest tube 702 includes opening 706 and drainage holes 708. In this figure the left side of the figure/device will be referred to as the "chest end". The opposite end of the device/figure will be referred to as the "outside end". Blood clots or other clogs 710 are shown here also. When clots/clogs are present in a chest tube, the chest tube clearing component of the chest drainage system 712 may be introduced into the chest tube as shown in FIG. 7B. Chest tube clearer 712 may be introduced via a Y-adapter at the chest tube/drainage tube interface. Alternatively, chest tube clearer may be incorporated into chest tube 702. The chest tube clearer may or may not be moveable within the chest tube.

Chest tube clearer 712 includes inner shaft or wire 716, and balloon 714 connected to the inner shaft, as shown in FIG. 7C. Balloon 714 is inflated via an inflation lumen that is fluidly connected to the inside of the balloon, runs through the shaft, and terminates outside of the patient. The balloon can be inflated and deflated via the inflation lumen from outside the patient. Inflation/deflation can be performed with a syringe, inflation device, manually or automatically. Balloon inflation pressure is about 10 psi to about 400 psi. Alternatively balloon inflation pressure is about 10 psi to about 50 psi. Alternatively balloon inflation pressure is about 50 psi to about 100 psi. Alternatively balloon inflation pressure is about 100 psi to about 200 psi. Alternatively balloon inflation pressure is about 200 psi to about 400 psi.

FIG. 7C shows balloon 714 at the initial stage of inflation. The balloon of the chest tube clearer is designed to inflate first at or near the chest end of the chest tube. As balloon 714 is inflated further, the balloon inflates further within the chest tube, as is shown in FIG. 7D. The movement of the contents of the chest tube caused by the inflation of the balloon help move clots and/or clogs within the chest tube out of the patient and out of the chest tube. FIG. 7E shows a fully inflated balloon. The balloon is then deflated which allows the blood to again drain freely from the chest through the chest tube to the drainage tube.

The balloon can be any effective length. The balloon can be around as long as the chest tube, for example up to around 50 cm long, or may be much shorter, for example around 10 cm long. The balloon may be inflated with air, gas, liquid, or any appropriate fluid.

The balloon may be manufactured out of either compliant or non-compliant material, or a combination of both. In a preferred embodiment, the OD of the inflated balloon is approximately the same size as the ID of the chest tube, however, the OD of the inflated balloon may be smaller or larger than the ID of the chest tube. The average OD of the deflated balloon is designed to fit easily through the chest tube. Preferably, the average OD of the deflated balloon is significantly smaller than the ID of the chest tube, so that blood and fluids can easily drain between the two when the chest tube clearer is in place within the chest tube. Vacuum may be applied to the balloon to reduce the deflated OD of the balloon. For example, the OD of the inflated balloon and the ID of the chest tube may be from around 8 mm to around 9 mm, and the average OD of the deflated balloon may be around 1 mm to around 2 mm. In another example, the OD of the inflated balloon and the ID of the chest tube may be around 4.5 mm to around 5.5 mm, and the average OD of the deflated balloon may be around 1 mm to around 2 mm.

The balloon may be designed to inflate closer to the chest end of the chest tube first by placement of the inflation hole, or the hole which fluidly communicates the interior of the balloon with the inflation lumen. The inflation hole may be close to the chest end of the chest tube clearer. Alternatively there may be multiple inflation holes, the largest of which is nearer the chest end of the chest tube clearer. The balloon may also be folded into a shape that encourages the chest end to inflate first. For example, the chest end of the balloon may be wrapped less tightly than the rest of the balloon. Specific folding geometries may be utilized. For example, pleated and/or folded and/or spiral folded balloons may be used. Some of the specific folding geometries may increase the unfolding pressure as well as exert a spiral motion, or torsional, force upon any clots/clogs in the chest tube, which may help clear the chest tube. The chest end of the balloon may also be larger, or more compliant than the rest of the balloon to encourage inflation there first. The balloon may require a relatively high pressure to open, or overcome the folding/compression, for example, about 5 psi to about 30 psi. This along with an inflation hole nearer the chest end of the chest tube clearer, will force the chest end of the balloon to inflate first. Note that the pressure to open the balloon and the pressure to inflate the balloon may be different pressures. Opening the balloon requires overcoming the folding, compression or other initial inflation pressure of the balloon. The inflation pressure of the balloon is the pressure used to keep the entire balloon open, and possibly exert force onto surrounding materials, such as clots, etc.

FIGS. 8A-8D show another embodiment of the chest tube clearer. In this embodiment, there are multiple balloons rather than one balloon. FIG. 8A shows the chest tube clearing device placed within the chest tube. The balloons of the chest tube clearing device are not inflated and there is space between the outside of the chest tube clearer and the inside of the chest tube for blood/fluids to flow.

FIG. 8B shows first balloon 802 inflated within the chest tube.

FIG. 8C shows second balloon 804 inflated. This figure shows first balloon 802 still inflated, but it is also possible that first balloon 802 deflates after second balloon 804 is inflated.

FIG. 8D shows multiple balloons inflated. The balloons are inflated in order, or sequentially, from the chest end of the chest tube toward the outside end of the chest tube. The balloons may inflate within the entire length of the chest tube, or just a portion of the length of the chest tube. In this way, clots and/or clogs are pushed out of the chest tube and out of the patient into the drainage tube. The balloons may also be inflated in any other preferred order.

The multiple balloons in this embodiment may be inflated via multiple inflation lumens, or one inflation lumen. There may be one, two, three or more balloons. Balloon length may be as short as around 1 cm or as long as around 20 cm.

FIGS. 9A-9D show another embodiment of the chest tube clearer. In this embodiment, the balloon, or balloons, are repeatedly inflated and deflated. This action may apply to any of the embodiments herein. In this manner, the chest tube clearer can break up the clots/clogs when inflated, and allow blood and fluids to flow through the chest tube when deflated. The balloon(s) may or may not inflate preferentially from the chest end in toward the outside end. The balloon(s) may alternatively inflate and deflate all at once, or relatively all at once, along the length of the chest tube. In this way, the balloon(s) may pulse, or even vibrate or flutter within the chest tube to clear the chest tube of clots/clogs. The balloon(s) may also be inflated to a relatively low pressure, so that it/they are slightly lax, and flutter naturally. Any of these or other inflation/deflation programs may be controlled by a controller. For example, the pulse rate, balloon inflation time, balloon deflation time, etc. may be controlled by a controller.

FIG. 10 shows an embodiment of the chest tube clearer with multiple balloons. In this embodiment, shaft 1002 includes balloon inflation opening 1004 which is relatively near the chest end of the chest tube clearing device. The multiple balloons are connected by lumens or channels 1006 which allow air and/or fluid to flow from the first balloon to the second balloon etc. In this embodiment, the first balloon, the balloon closest to the chest end of the chest tube, inflates first. When the pressure within the first balloon reaches a certain threshold, the inflation fluid "leaks" into the second balloon via channel 1006 to inflate the second balloon after the first balloon. When the pressure within the second balloon reaches a certain threshold, the inflation fluid "leaks" into the third balloon, and so on. In this way, the balloons in this embodiment inflate closer to the chest end first, and closer to the outside end last.

FIG. 11 is another embodiment of the chest tube clearer with multiple balloons. In this embodiment, shaft 1002 terminates inside the first balloon, with open end 1102. Shaft 1002 may be mounted on wire 1104 for stability, so that the first balloon may be bonded to the end of wire 1104. This allows for a large balloon inflation opening, 1102, without sacrificing rigidity of the shaft.

Note that any of the embodiments of the chest tube clearer can intermittently close off the chest tube so that any negative pressure applied to the drainage tube will not be applied directly to the chest cavity. This allows higher negative pressures to be used to drain the drainage tube. In other words, the balloon(s) in the chest tube clearer can essentially serve the function of valve 208 in FIG. 2A.

Other embodiments of the chest drainage system are envisioned. For example:

the chest tube itself may be tapered so that the diameter of the inside of the tube gets smaller on one end or the other.

A wire, filament, or other disrupter of any sort may be used to dislodge clots/clogs in the chest tube. The movement, vibration, rotating/screw, sliding etc. of this disrupter may be automated, either on a time schedule, or in response to the system sensing a clog in the chest tube.

Other balloon configurations are envisioned. Some of these are shown in FIG. 12.

The chest tube itself could be configured to vibrate, or move in some manner to dislodge clots.

The negative pressure (suction) exerted on the chest tube by the chest drainage system could be pulsated or applied in a patterned or random way.

A catheter, tube, and/or lumen may be used to spray fluid and/or drug, such as saline, heparin etc. into the chest tube.

The inside of the chest tube may be coated with a slippery and/or hydrophobic substance and/or drug, such as Teflon, silicone, heparin, etc. The inside of the chest tube may be textured in a way to increase flow, such as with dimples similar to those on the outside of a golf ball.

A bellow or bellows may be placed or incorporated into the inside of the chest tube.

The diameter of the chest tube may change over time. For example, the chest tube diameter may be designed to increase or decrease occasionally to break up clots/clogs. This change in diameter may occur on a regular schedule or in response to detecting a clot situation. The diameter change may fluctuate constantly.

The temperature of the chest tube may be increased or reduced from ambient and/or patient temperature.

A tube may be inserted or incorporated into the chest tube which has an outer diameter close to the inner diameter of the chest tube. This inner tube may have holes in it which match the location of the holes of the chest tube. The inner tube may be moved relative to the chest tube to break up clots, particularly at the chest tube holes.

The chest tube may incorporate inner valves.

Air bubbles may be introduced into the chest tube to help clear the chest tube.

A wire, filament thread, etc. may cycle through the chest tube as is shown in FIG. 13.

A pre-shaped corkscrew wire, such as made from Nitinol, stainless steel, metal, polymer or other suitable material, may be deployed to corkscrew along the inner wall of the chest tube, then pulled axially to scrape/remove any clots adhered to the wall of the chest tube. The pre-shaped wire cross section may be designed such that a shoveling/scooping/peeling action occurs as the wire is pulled axially along the length of the chest tube. The pre-shaped wire may also remain stationary and rotated to remove the clot from the chest tube similar to an auger. The pre-shaped wire may form a variable diameter along the length of the tube, such that sections of the pre-shaped wire touch the inner wall of the tube and other sections do not. The wire could be rotated and axially moved along the wall of the tube to urge the clot to move through the tube to the collection chamber. The cross section of the "wire" of the corkscrew wire may be round, flat, or other suitable shape.

A ball or cage may be incorporated into the chest tube at the chest end of the chest tube to help blood/fluids enter the tube.

The chest tube may have multiple arms/lumens at the chest end to help blood/fluids enter the tube.

The chest tube may incorporate a steering mechanism, for example a curved mandrel, to help steer it to better collect blood/fluids.

The chest tube may incorporate a weight at the chest end to help it drain pooled blood/fluids.

The chest tube may include an anchor at the chest end to anchor it to the inside of the chest wall. For example, see FIG. 14.

Detecting Infection

In some embodiment of the chest drainage system, the collection container, or other component in the system, may include the ability to detect bacteria, blood and/other substances in the drainage fluid using UV/light spectroscopy. For example the collection container may include an optically clear section which is preferably incorporated into an outside wall of the container, and a reflector section, which is preferably on, or incorporated into, an inner wall of the container. "Optically clear" here means able to transmit light at the needed analysis wavelength(s) through the optically clear section. Preferably the optically clear section made of a material which is able to transmit UV light, such as polymethylmethacrylate, polystyrene, acrylic, quartz, etc. The wall thickness may need to be thin enough to allow the appropriate UV wavelength(s) to be transmitted through the optically clear section. For example, the thickness of the optically clear section may be from around 0.5 mm to around 0.7 mm thick. Alternatively the thickness of the optically clear section may be from around 0.5 mm to around 0.6 mm thick. Alternatively the thickness of the optically clear section may be from around 0.6 mm to around 0.7 mm thick. Alternatively the thickness of the optically clear section may be less than around 0.7 mm thick.

A UV/light transmitter/receiver transmits UV or other wavelength light in the appropriate wavelength through optically clear section, through the fluid in the collection container, to the reflector in the collection container. The UV/light transmitter/receiver may be incorporated into, or connected to, the controller component of the chest drainage system. The light is reflected back to the UV/light receiver which then transmits the collected data to the controller for signal analysis. More than one UV/light wavelength may be analyzed either simultaneously or serially. Light outside of the UV range may be used in addition to light within the UV range. The volume of fluid physically between the transmission and receiving of the light is preferably maximized for a stronger signal reflecting the concentration of one or more substances in the fluid. The transmitter/receiver may be located in any area of the collection container. The receiver may be in a different location than the transmitter and the reflector may or may not be necessary nor present. In embodiments where the fluid in the collection container is frequently emptied, the UV/light absorption measurements can be collected over time and increases and/or decreases in the level of one or more substances in the drainage fluid can be tracked over time, in essentially, or nearly, real time. This is particularly important in identifying infection quickly. The UV/light detection may also be performed elsewhere in the chest drainage system, including in the drainage tubing, the chest tube, the valve device, a separate sampling area etc.

Infection may be identified by analyzing the fluid for bacteria, red blood cells, and plasma and/or white blood cells using UV/light spectroscopy. The presence of plasma/white blood cells and/or bacteria in fluid are both indicators of infection. The presence of red blood cells may not be indicative of infection. Therefore it is desirable to distinguish between red blood cells and bacteria/plasma/white blood cells in the drained fluid. Since the spectroscopic signature for red blood cells differs significantly from those of either bacteria or plasma/white blood cells, at a wavelength of about 414 nm, the signal for red blood cells can be separated from those of bacteria and/or plasma/white blood cells, and an infection can be identified by analyzing the absorption of light at this wavelength. Because the signature for plasma and bacteria differ from each other at the wavelengths of 260 nm and 280 nm, these wavelengths can be used to distinguish between plasma and bacteria. However, it is likely that both plasma and bacteria may be present during an infection.

Other wavelengths and other technologies may also be used to detect various substances in the drained fluid. UV/light absorption may also be used to detect turbidity. A dye or drug or reactive substance may also be introduced into the system, or be coated on the inside of the system, collection container, etc, to react with a substance in the drained fluid to aid in analysis.

Example of Data Processing System

Figure 15:
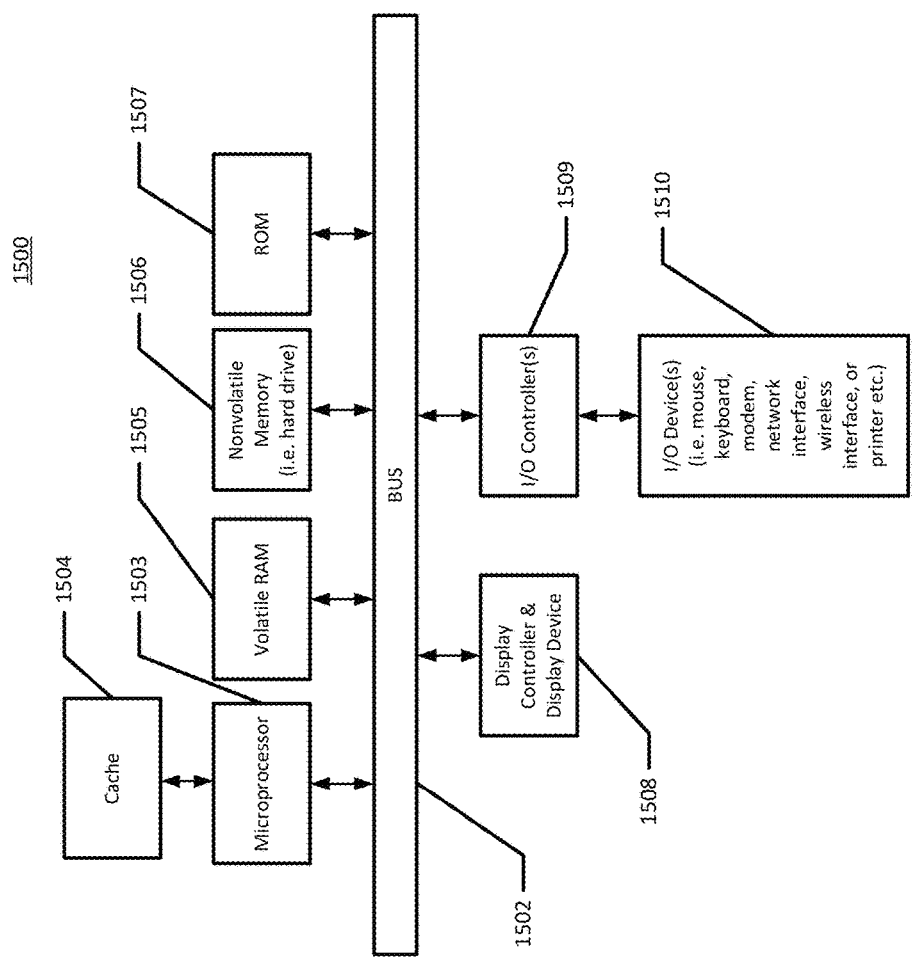
FIG. 15 shows a block diagram of a data processing system, which may be used with any embodiments of the invention.

FIG. 15 is a block diagram of a data processing system, which may be used with any embodiment of the invention. For example, the system 1500 may be used as part of the controller. Note that while FIG. 15 illustrates various components of a computer system, it is not intended to represent any particular architecture or manner of interconnecting the components; as such details are not germane to the present invention. It will also be appreciated that network computers, handheld computers, mobile devices, tablets, cell phones and other data processing systems which have fewer components or perhaps more components may also be used with the present invention.

As shown in FIG. 15, the computer system 1500, which is a form of a data processing system, includes a bus or interconnect 1502 which is coupled to one or more microprocessors 1503 and a ROM 1507, a volatile RAM 1505, and a non-volatile memory 1506. The microprocessor 1503 is coupled to cache memory 1504. The bus 1502 interconnects these various components together and also interconnects these components 1503, 1507, 1505, and 1506 to a display controller and display device 1508, as well as to input/output (I/O) devices 1510, which may be mice, keyboards, modems, network interfaces, printers, and other devices which are well-known in the art.

Typically, the input/output devices 1510 are coupled to the system through input/output controllers 1509. The volatile RAM 1505 is typically implemented as dynamic RAM (DRAM) which requires power continuously in order to refresh or maintain the data in the memory. The non-volatile memory 1506 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 15 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 1502 may include one or more buses connected to each other through various bridges, controllers, and/or adapters, as is well-known in the art. In one embodiment, the I/O controller 1509 includes a USB (Universal Serial Bus) adapter for controlling USB peripherals. Alternatively, I/O controller 1509 may include IEEE-1394 adapter, also known as FireWire adapter, for controlling FireWire devices, SPI (serial peripheral interface), I2C (inter-integrated circuit) or UART (universal asynchronous receiver/transmitter), or any other suitable technology.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the figures can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

The processes or methods depicted in the preceding figures may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

What is claimed is:

1. A drainage assembly, comprising:
a suction device configured to generate a negative pressure;
a lumen body fluidly coupled to the suction device and further configured for coupling to a tube which is insertable into a patient body;
a valve tube in fluid communication with the lumen body;

a valve assembly fluidly coupled to the valve tube, wherein the valve assembly includes at least a first valve having a closed configuration where the negative pressure generated by the suction device is maintained within the lumen body, and the first valve further having an open configuration where the negative pressure draws air from an environment and through the lumen body; and a controller in communication with the valve assembly, wherein the controller is programmed to actuate the first valve into the open configuration automatically on a periodic, fixed time interval basis.

2. The assembly of claim 1 wherein the tube comprises a chest tube having a first lumen body.

3. The assembly of claim 1 wherein the lumen body comprises a drainage tube.

4. The assembly of claim 1 further comprising a drainage container in fluid communication with the lumen body.

5. The assembly of claim 1 wherein the valve assembly further comprises a second valve having a closed configuration which prevents flow from the tube into the lumen body, and the second valve further having an open configuration where the negative pressure is maintained within the tube.

6. The assembly of claim 5 wherein second valve is actuatable into its closed configuration when the first valve is actuated into its open configuration.

7. The assembly of claim 1 wherein the first valve is also manually actuatable.

8. The assembly of claim 1 wherein the controller is programmed to continuously monitor a pressure detected by a pressure sensor.

9. The assembly of claim 1 wherein the controller is programmed to intermittently actuate the first valve into its closed configuration.

10. The assembly of claim 1 further comprising a pressure sensor in proximity to the suction device and configured to detect a pressure within the lumen body.

11. The assembly of claim 1 wherein the controller is incorporated into the suction device.

12. The assembly of claim 1 wherein the valve assembly is incorporated into the suction device.

13. A method for draining a body lumen, comprising:
drawing a fluid from a patient body via negative pressure such that the fluid is drawn through a lumen body in fluid communication with a tube which is insertable into the patient body;
actuating a valve assembly coupled to a valve tube in fluid communication with the lumen body such that at least a first valve in the valve assembly actuates from a closed configuration, where the negative pressure is maintained within the lumen body, and into an open configuration automatically on a periodic, fixed time interval basis, where the negative pressure draws air from an environment and through the lumen body; and
clearing an obstruction from the lumen body via the air introduced into the lumen body.

14. The method of claim 13 wherein drawing the fluid from the patient body comprises applying the negative pressure to the tube.

15. The method of claim 13 wherein prior to actuating a valve assembly, further comprising monitoring via a pressure sensor for a decrease in the negative pressure as indicative of an obstruction within the body lumen.

16. The method of claim 15 wherein monitoring via a pressure sensor comprises continuously monitor the pressure.

17. The method of claim 13 wherein actuating a valve assembly comprises actuating via a controller in communication with a pressure sensor, wherein the controller is programmed to sense for a decrease in the negative pressure indicative of the obstruction within the lumen body.

18. The method of claim 13 further comprising introducing the tube into the patient body prior to applying the negative pressure.

19. The method of claim 13 further comprising draining the fluid into a drainage container in fluid communication with the lumen body.

20. The method of claim 13 wherein actuating a valve assembly further comprises actuating a second valve from an open configuration, where the negative pressure is maintained, and into a closed configuration which prevents flow between the tube and the lumen body.

21. The method of claim 13 wherein the first valve is actuatable automatically via a controller or manually actuatable.

22. The method of claim 13 wherein actuating a valve assembly comprises intermittently actuating the first valve into its closed configuration.

23. The method of claim 13 further comprising detecting a pressure within the lumen body via a pressure sensor in proximity to the suction device prior to clearing an obstruction from the lumen body.

24. The method of claim 13 further comprising increasing a magnitude of the negative pressure while the first valve is in the open configuration via a controller.

* * * * *